(12) United States Patent
Fournet

(10) Patent No.: US 7,210,934 B2
(45) Date of Patent: May 1, 2007

(54) DENTAL PROSTHESIS MADE OF COMPOSITE MATERIAL AND METHOD FOR MAKING SAME

(76) Inventor: Alain Fournet, 14, Rue Sainte-Aubierge, Saint-Augustin (FR) F-77515

( * ) Notice: Subject to any disclaimer, the term of this patent is extended or adjusted under 35 U.S.C. 154(b) by 419 days.

(21) Appl. No.: 10/484,266

(22) PCT Filed: Jul. 16, 2002

(86) PCT No.: PCT/FR02/02531

§ 371 (c)(1),
(2), (4) Date: Jan. 20, 2004

(87) PCT Pub. No.: WO03/007837

PCT Pub. Date: Jan. 20, 2003

(65) Prior Publication Data

US 2004/0197739 A1    Oct. 7, 2004

(30) Foreign Application Priority Data

Jul. 18, 2001  (FR) .................................. 01 09595

(51) Int. Cl.
*A61C 5/08* (2006.01)
*A61C 5/10* (2006.01)
(52) U.S. Cl. ................ 433/223; 433/228.1; 433/222.1; 427/2.29
(58) Field of Classification Search ................ 433/206, 433/212.1, 222.1, 228.1; 106/35; 427/2.1, 427/2.19
See application file for complete search history.

(56) References Cited

U.S. PATENT DOCUMENTS

| 5,106,303 | A | * | 4/1992 | Oden et al. .................. 433/223 |
| 5,697,785 | A | * | 12/1997 | Delahaye .................. 433/212.1 |
| 5,843,348 | A | * | 12/1998 | Giordano ...................... 264/19 |
| 6,533,969 | B1 | * | 3/2003 | Daskalon et al. .............. 264/16 |
| 6,648,645 | B1 | * | 11/2003 | MacDougald et al. ....... 433/223 |
| 2002/0197583 | A1 | * | 12/2002 | Jones et al. .............. 433/202.1 |
| 2005/0127544 | A1 | * | 6/2005 | Brodkin et al. ................ 264/16 |

* cited by examiner

*Primary Examiner*—Cary E. O'Connor
(74) *Attorney, Agent, or Firm*—Young & Thompson

(57) ABSTRACT

The invention concerns dental prostheses. It concerns a method for making a dental prosthesis of composite material by forming an adhesive interface between a metallic support and a cured ceramic material less than 3 mm thick, forming an intermediate interface by treating the surface of a ceramic material with an organic silane, and forming an adhesive interface of the reconstructing mass by treating the silane with an adhesive material compatible with the composite material. The intermediate interface is prepared by an etching operation in conditions liable to form cracks or embrittle the ceramics. The invention is applicable to dental prostheses made of composite material.

16 Claims, No Drawings

DENTAL PROSTHESIS MADE OF COMPOSITE MATERIAL AND METHOD FOR MAKING SAME

BACKGROUND OF THE INVENTION

The present invention relates to a method of making a dental prosthesis comprising a reconstruction mass fixed to a metal support and formed essentially of a composite material containing a polymer binder having an inorganic filler dispersed therein, and the invention also relates to a dental prosthesis of this type.

Before describing the invention, it is appropriate to specify the terminology used in the present specification and which corresponds to that of the person skilled in the art.

Care of the teeth comprises essentially the field of repair and reconstruction proper of the teeth, and the field of prosthetic reconstructions. The term "repairs" cover fillings (classes I to V), inlays, and onlays.

Prosthetic reconstructions are prostheses that may be fixed or removable. Usually, such reconstructions have a metal portion and apply to a plurality of teeth, although they can also apply to a single tooth only. They are fixed to one or more teeth. They may also be fixed to one or more implants. Such reconstructions are also referred to as "prostheses" in the present specification.

The invention relates to prosthetic reconstructions of the fixed type. In general, these fixed type reconstructions comprise a metal support made by casting a metal or an alloy, and a reconstruction mass that is fixed to the support and that may be made of various different materials. The materials in most widespread use for such fixed reconstructions are ceramic materials and new-generation composite materials.

The term "new-generation composite material" is used to designate a polymerized composite material having bending strength of not less than 100 megapascals (MPa) and Vickers hardness of not less than 450 newtons per square millimeter ($N/mm^2$). As examples of such materials, mention can be made "Columbus" and "Cristobal" from the supplier IDR.

Ceramic prosthetic reconstructions present great rigidity and low bending strength, and they must be fixed on teeth that are solidly consolidated. From the point of view of preparation, protocols for constructing such ceramic prosthetic reconstructions are simple and well established, and they enable practically all prosthesis technicians to obtain a very high success rate. From the point of view of clinical results, it is found that people fitted with such large-sized ceramic reconstructions often encounter problems in the periodontium (alveolysis) possibly with thickening of the alveolodental ligament, and frequently with more or less pronounced mobility of the teeth and fractures. The failure rate due to the above-mentioned problems is significant.

Prosthetic reconstructions made of new-generation composite materials raise an opposite problem. From the point of view of clinical results, these prosthetic reconstructions give excellent results, as has been proved by numerous clinical trials. From the preparation point of view, although it is known how to make dental prostheses having a reconstruction mass that is constituted essentially out of new-generation composite material, as described in document WO 95/06453, such prosthetic reconstructions raise problems of preparation since it is difficult to fix the reconstruction mass to the metal support. Although experienced prosthetic technicians can obtain excellent results in reproducible manner for such fixing, only about one-tenth of prostheses technicians are capable of reliably achieving the bonding needed for fixing such prostheses. It can thus be considered that making prostheses out of new-generation composite materials suffers from the drawback of requiring highly experienced technicians.

SUMMARY OF THE INVENTION

The invention relates to a solution of this problem of making prosthetic reconstructions out of new-generation composite material. Since this is a problem faced by technicians, the invention thus relates to prostheses made by prosthesis technicians, prostheses that can be processed in firing and polymerizing ovens, as contrasted with work done in the mouth.

More precisely, the invention relates to making means available that enable practically all prosthesis technicians to make prostheses out of new-generation composite material.

Ceramic prostheses have already been repaired in the mouth using new-generation composite materials. Good results have often been obtained. Nevertheless, prostheses repaired in that way do not possess the advantage of a prosthesis in which the entire reconstruction mass is made of a composite material, since the additional composite material is fixed on a rigid body constituted by the ceramic material. The thickness of the ceramic material is relatively large, of millimeter order at least, so the mechanical strength and the rigidity of the prosthesis are determined by the ceramic material, with the prosthesis presenting the same behavior as a ceramic prosthesis in clinical trials.

During such a repair, the surface of the ceramic portion of the prosthesis to be repaired is treated, e.g. by etching in a manner that is compatible with work in the mouth, so as to enable a silane to be applied subsequently. A bonding or "keying" layer of composite material is then applied prior to a plurality of layers of composite material, each of which is subjected to photopolymerization. All of those operations must be performed at low temperature in the mouth of the patient.

Etching is chemical treatment of the surface and comprises attacking the surface of the ceramic material with strong acid solutions, e.g. of hydrofluoric acid. In general, the ceramic material comprises a vitreous phase bonding a crystalline phase. The etching preferentially attacks either the vitreous phase or the crystalline phase, and in either case leads to a high degree of surface irregularity.

It is known in general manner that the bonding area can be increased by a sandblasting operation (not possible for work in the mouth). In such sandblasting, a powder, e.g. grains of alumina or microbeads, is projected onto the surface. This treatment gives rise to surface irregularities. It is sometimes observed that sandblasting leads to cracks being created in the surface of the ceramic material. When etching is applied after sandblasting, it has the drawback of sometimes leading to propagation of cracks that were started during sandblasting.

Given that the ceramic material is very rigid, cracks are easily propagated therein. Consequently, when repairing ceramic materials with composite materials, action is restricted to conditions which avoid initial crack formation and the propagation of such cracks.

For example, the article entitled "La vitrocéramique" by F. Lelièvre in Art et technique dentaire, Vol. 5, No. 2, April 1994 states that "etching is a source of weakening of the ceramic base". Furthermore, the article by B. Terrié entitled "Céramique et collage" in Art et technique dentaire, Vol. 1, No. 4, August 1990 states that surface irregularities formed by sandblasting "generate cracks which lead to breaks by propagation after etching".

As mentioned above, experience has shown that the portion of a prosthesis of new-generation composite material that is the most difficult to make is the bonding interface between the metal support and the reconstruction mass. Given the above-mentioned problems raised by such bonding layers, consideration might be given to applying the teaching of the above-mentioned technique for repairing ceramic materials by means of composite materials in order to find a solution to the problem. Thus, it might be thought that a metal bonding structure could be created made out of a ceramic material, and then the reconstruction mass could be bonded to the ceramic material by appropriate sandblasting and etching operations. However, as shown in the prior art, it can be expected that such a solution would lead to cracks in the resulting structure.

The invention relates to a solution of this type, performed under special conditions such that these problems are solved or do not even arise.

DESCRIPTION OF THE PREFERRED EMBODIMENTS

More precisely, according to the invention, a prosthesis is made by initial operations of forming a metal bonding interface out of a ceramic material fired at high temperature, and having in conventional manner very good metal-bonding strength. According to the invention, the thickness of the ceramic material is very small, e.g. lying in the range 0.05 millimeters (mm) to 0.3 mm, so that any cracks and crack starters that might be created have no repercussions on the remainder of the prosthesis.

According to the invention, the problem of making composite material prostheses, i.e. of bonding a composite material onto a metal support, is replaced by the problem of bonding a composite material onto a thin layer of ceramic material. In the invention, this bonding can be achieved with a practically maximum success rate by practically all prosthesis technicians.

Thus, the bonding between the ceramic and the composite material is obtained firstly by forming an irregular surface on the face of the ceramic material facing away from the bonding interface between the ceramic and the metal, then by forming an intermediate interface using an organic silane, and then by forming a bonding interface between the composite material and the organic silane, thus enabling a reconstruction mass to be built on the composite material.

The essential characteristics of the invention are thus firstly forming a very thin metal-bonding interface out of a ceramic material that has a highly irregular surface, and then in making a bonding interface for the reconstruction mass which does not require any difficult operation to be performed and which can thus be performed by practically any prosthesis technician.

More precisely, the invention provides a method of making a dental prosthesis of the type comprising a reconstruction mass fixed to a metal support, the reconstruction mass being formed, at least for the most part, out of a composite material containing a polymer binder in which an inorganic filler is dispersed, the method being of the type which comprises: forming a metal-bonding interface on the metal support; forming an intermediate interface; and forming a reconstruction mass bonding interface, and, according to the invention, the metal bonding interface is formed by at least one layer of ceramic material fixed to the metal by firing, the ceramic material of the layer at least being of thickness less than or equal to 0.3 mm; the intermediate interface is formed by treating the surface of the ceramic material facing away from the metal with an organic silane; the reconstruction mass bonding interface is formed by treating the surface of the intermediate interface with a bonding composite material; and prior to treatment with an organic silane, the forming of the intermediate interface includes at least one etching operation. The etching operation may be performed even under conditions that are likely to form cracks or to weaken a ceramic body.

In an advantageous implementation, prior to treating the surface of the ceramic material facing away from the metal with an organic silane, the ceramic material is subjected to an operation of sandblasting and cleaning prior to etching.

In another advantageous implementation, the metal-bonding interface is formed by forming at least two layers of ceramic opaque. The layers of ceramic opaque preferably comprise at least one aluminosilicate or vitroceramic. In an advantageous variant, at least the surface layer of the ceramic material is made from a slip of ceramic opaque containing inorganic particles, e.g. glass particles. For this purpose, it is possible to use the substances in the "Opaque Finesse" kit from Dentsply or the "Biopaque" kit from Biodent. It is also possible to use 99.7% corundum particles of 50 micrometer (μm), 125 μm, or 250 μm size.

Preferably, the thickness of the ceramic material is less than 0.2 mm.

Preferably, the organic silane treatment of the surface of the ceramic material facing away from the metal is performed using a methacryloxypropyltrimethoxy-silane.

The invention also provides a prosthesis of the type comprising a reconstruction mass fixed to a metal support, the reconstruction mass being formed, at least for the most part, out of a composite material containing a polymer binder having an inorganic filler dispersed therein, the prosthesis comprises: a metal bonding interface for bonding to the metal support; an intermediate interface; and a reconstruction mass bonding interface, which are such that the metal bonding interface is formed between the metal of the metal support and a layer of ceramic material fixed by firing and of thickness less than or equal to 0.3 mm; the intermediate interface is formed between a layer of ceramic material and an organic silane fixed by reaction between a silane group and the surface of the ceramic material facing away from the metal; and the composite material bonding interface is formed between organic groups of an organic silane and a material that is compatible with the composite material.

Preferably, the irregularity of the intermediate interface is such that its developed area is at least 1.4 times its projection onto its plane. In an embodiment, the surface portion of the ceramic material facing away from the metal contains particles of a vitreous material.

In an embodiment, the ceramic material comprises at least one element selected from an aluminosilicate and a vitroceramic.

The thickness of the ceramic material fixed by firing is preferably less than 0.2 mm. Thus, the ceramic material fixed by firing may present cracks without them having the slightest importance on the mechanical strength of the resulting prosthesis.

The essential advantage of the invention is that it enables such prostheses of composite material to be made not only by elite prosthesis technicians, but by practically the entire profession.

An example of making a prosthetic reconstruction out of composite material in accordance with the invention is described below.

In this implementation, the first operation comprises constructing a metal support in the form of a casting of "Esteticor Royal" metal from the suppliers Cendres et Métaux on a wax template at a temperature in the range 1345° C. to 1375° C. Thereafter, the metal support is subjected to oxidation at 960° C. for 5 minutes (min). Thereafter, the metal support is cleaned in steam or by ultrasound. Instead of being cast, the metal support could equally well be cut from a block.

The following stage comprises making the metal-bonding interface out of a ceramic material. This step comprises, for example, applying a first layer of ceramic opaque having a thickness of a few hundreds of a millimeter. The first layer of opaque may be a layer of "Biopaque Base" opaque from De Trey, with microparticles being dusted thereon. The microparticles are made of an aluminosilicate glass. The layer is subjected to firing, and then a second layer of "Biopaque" ceramic opaque from De Trey is applied in analogous manner and is dusted in microparticles that are normally intended to disperse light in order to provide advantageous effects in terms of appearance. In the context of the invention, the particles have the advantage of increasing surface irregularity. The second layer is then fired. The layers of ceramic material are fired at a temperature of about 970° C. to 980° C.

The high temperature operations are then over since the remainder of the method can be performed at a temperature close to ambient temperature.

Although the particles of the last layer of ceramic opaque give rise to a rough surface, it is advantageous to give the surface even greater irregularity by sandblasting, e.g. using particles of alumina. After cleaning, the surface irregularity is increased by etching. This can be performed, for example, by means of a 9.5% hydrofluoric acid solution for 4 min, or by means of a 4% hydrofluoric acid solution for 6 min, or by the "Super-Etch" solution of the "Porcelain System" kit from the supplier Mirage Dental Products. The surface of the ceramic material is finally treated by being rinsed in steam.

The intermediate interface is then made by applying an organic silane, e.g. a methacryloxypropyltrimethoxy-silane, applied by means of a brush. After drying, an organic bonding layer compatible with the new-generation composite material is applied. By way of example, it is possible to apply in succession two layers of a "One-Step" material from the supplier Bisco, each layer being polymerized for 30 seconds (s).

Thereafter, an adhesive or bonding liquid normally used with new-generation composite materials is applied, for example the "Columbus" adhesive liquid from the supplier IDR, which is photopolymerized for 75 s. Thereafter, the reconstruction mass is built up by applying the necessary number of layers of composite material, e.g. the "Columbus" material, using the protocol applicable to that material. More precisely, the reconstruction mass of composite material is preferably built up by photopolymerization, possibly with heating to a relatively low temperature, possibly in the range 60° C. to 80° C.

All of the operations undertaken from making the metal support to the end of building up the reconstruction mass are simple and easy for all prosthesis technicians to perform. In particular, it is well known how to make the metal bonding interface of ceramic material, and the entire construction of the metal bonding ceramic structure is within the competence of practically any prosthesis technician with a success rate equal to nearly 100%.

Although the use of an adhesive liquid is described, it will be understood that when the organic structural units of the silane are directly compatible with the composite material used, the composite material may be applied directly on the organic silane.

Tests have been performed to determine the bonding strength of the various layers to different materials under conditions that are comparable in order to be able to compare the results.

The bonding strength obtained between a new-generation composite material ("Columbus") and a metal support made by an experienced technician using established protocols commonly exceeds 20 MPa. However, it commonly happens that the value obtained by an inexperienced technician is less than 5 MPa, which value is quite insufficient. The bond obtained by the "Silicoater-Rocatec" technique does not exceed 7.5 MPa.

The bonding strength obtained between a metal an opaque ceramic material ("Biopaque") has a value of at least 40 MPa.

In the invention, the bonding strength between a composite reconstruction mass ("Columbus") and a ceramic material ("Biopaque") reproducibly exceeds 35 MPa.

For reference, the value of the composite-composite bond lies in the range 40 MPa to 50 MPa.

It can thus be seen that a technician implementing operations of a kind commonly performed using protocols that are well known can, without difficulty, easily obtain bonding strength that is always greater than 20 MPa in all of the interfaces of the prosthesis.

In the 1970s, only elite technicians were capable of making acceptable ceramic prosthesis. It took a few tens of years for techniques to be developed that enable all technicians to achieve success with all ceramic prostheses.

The present situation with composite material prosthesis is analogous to that with ceramic prostheses in the 1970s. The techniques of the invention make it possible to avoid such a period of a few tens of years of development, and all technicians can as from now succeed in making all composite material prostheses.

SUSCEPTIBILITY OF INDUSTRIAL APPLICATION

The method of the invention is suitable for making dental prostheses in the workshops of prosthesis technicians.

The invention claimed is:
1. A prosthesis comprising:
   a reconstruction mass fixed to a metal support, the reconstruction mass being formed, at least for the most part, out of a composite material containing a polymer binder having an inorganic filler dispersed therein;
   a metal bonding interface for bonding to the metal support; and
   a reconstruction mass bonding interface between organic groups of an organic silane and a material that is compatible with the composite material,
   wherein the metal bonding interface is formed between the metal of the metal support and a layer of ceramic material fixed by firing and of thickness less than or equal to 0.3 mm,
   wherein an intermediate interface is formed between the layer of ceramic material and an organic silane fixed by reaction between a silane group and the surface of the ceramic material facing away from the metal.

2. A prosthesis according to claim 1, characterized in that the thickness of the layer of a ceramic material fixed by firing is less than 0.2 mm.

3. A prosthesis according to claim 2, characterized in that the irregularity of the intermediate interface is such that its developed area is not less than 1.4 times its projection onto its plane.

4. A prosthesis according to claim 2, characterized in that the surface portion of the ceramic material on its side facing away from the metal contains particles of a vitreous material.

5. A prosthesis according to claim 2, characterized in that the ceramic material comprises at least one element selected from an aluminosilicate and a vitroceramic.

6. A prosthesis according to claim 1, characterized in that the irregularity of the intermediate interface is such that its developed area is not less than 1.4 times its projection onto its plane.

7. A prosthesis according to claim 6, characterized in that the surface portion of the ceramic material on its side facing away from the metal contains particles of a vitreous material.

8. A prosthesis according to claim 6, characterized in that the ceramic material comprises at least one element selected from an aluminosilicate and a vitroceramic.

9. A prosthesis according to claim 1, characterized in that the surface portion of the ceramic material on its side facing away from the metal contains particles of a vitreous material.

10. A prosthesis according to claim 9, characterized in that the ceramic material comprises at least one element selected from an aluminosilicate and a vitroceramic.

11. A prosthesis according to claim 1, characterized in that the ceramic material comprises at least one element selected from an aluminosilicate and a vitroceramic.

12. A method of making a dental prosthesis of the type comprising a reconstruction, mass fixed to a metal support, the reconstruction mass being formed, at least for the most part, out of a composite material containing a polymer binder in which an inorganic filler is dispersed, the method being of the type which comprises:
   forming a metal-bonding interface on the metal support;
   forming an intermediate interface; and
   forming a reconstruction mass bonding interface, the method being characterized in that:
   the metal bonding interface is formed by at least one layer of ceramic material fixed to the metal by firing, the ceramic material of the layer at least being of thickness less than or equal to 0.3 mm;
   the intermediate interface is formed by treating the surface of the ceramic material facing away from the metal with an organic silane;
   the reconstruction mass bonding interface is formed by treating the surface of the intermediate interface with a bonding composite material; and
   prior to treatment with an organic silane, the forming of the intermediate interface includes at least one etching operation.

13. A method according to claim 12, characterized in that forming the metal bonding interface comprises forming at least two layers of ceramic opaque.

14. A method according to claim 13, characterized in that the ceramic material forming the metal bonding interface is obtained by using a ceramic opaque slip containing particles of a glass at least on its side opposite from the metal bonding interface.

15. A method according to claim 12, characterized in that, prior to etching, forming the intermediate interface includes at least one operation of sandblasting and cleaning.

16. A method according to claim 12, characterized in that the treatment of the surface of the ceramic material facing away from the metal with an organic silane is performed with methacryloxypropyltrimethoxysilane.

* * * * *